United States Patent [19]
Krivoshlykov

[11] Patent Number: 6,016,197
[45] Date of Patent: Jan. 18, 2000

[54] COMPACT, ALL-OPTICAL SPECTRUM ANALYZER FOR CHEMICAL AND BIOLOGICAL FIBER OPTIC SENSORS

[75] Inventor: Sergej G. Krivoshlykov, Moscow, Russian Federation

[73] Assignee: CeramOptec Industries Inc., East Longmeadow, Mass.

[21] Appl. No.: 08/934,236

[22] Filed: Sep. 22, 1997

Related U.S. Application Data

[63] Continuation of application No. 08/519,824, Aug. 25, 1995, abandoned.

[51] Int. Cl.[7] ........................................... G01B 9/02
[52] U.S. Cl. .............................. 356/345; 356/346
[58] Field of Search ........................ 356/345, 346; 250/227.19, 227.27; 385/12, 14

[56] References Cited

U.S. PATENT DOCUMENTS

| | | | |
|---|---|---|---|
| 3,924,952 | 12/1975 | Maréchal et al. | 356/346 |
| 4,779,984 | 10/1988 | Cook | 356/346 |

OTHER PUBLICATIONS

D.D. Mareenac & J.E. Carroll, "Maximum–Entropy Optical Spectrum Analyzer", Optics Letters 20 1074–6 (1995).

Marketing Brochure—"S1000 Miniature Fiber Optic Spectrometer" Ocean Optics Inc.

*Primary Examiner*—Samuel A. Turner
*Attorney, Agent, or Firm*—Bolesh J. Skutnik; B J Associates

[57] ABSTRACT

An optical spectrum analyzer based on optical processing of the far field interference pattern from two beams irradiated by light transmitting waveguides is described. The spectrum analyzer can operate in UV, VIS, NIR and MIR ranges of spectrum and it can be based on either optical fibers (multimode or single-mode) or integrated optical waveguides. It has many important applications, for example, as a simple, compact and inexpensive spectrum analyzer used with fiber optic chemical and biological sensors.

20 Claims, 2 Drawing Sheets

COMPACT, ALL-OPTICAL SPECTRUM ANALYZER FOR CHEMICAL AND BIOLOGICAL FIBER OPTIC SENSORS

This is a continuation of application Ser. No. 08/519,824, filed Aug. 25, 1995, now abandoned.

BACKGROUND OF THE INVENTION

1. Field of the Invention

The present invention relates to optical spectrometers and in particular to a new class of flexible fiber optic or integrated optical spectrum analyzers for UV, VIS, NIR and MIR ranges of spectrum which do not require dispersion gratings, expensive mechanical parts or additional optical sources. The spectrum analyzer can be used with or in fiber optic chemical and biological sensors to monitor samples in situ instead of testing them in the laboratory.

2. Information Disclosure Statement

Optical spectrum analyzers have many important applications for monitoring the spectra of optical signals. They can be used, for example, in various fiber optic chemical and biological sensor systems designed to detect concentrations of different species. Each specific species to be detected has a certain characteristic absorption line, a so called fingerprint, which can be selected with the help of spectrum analyzers. Intensity of this selected spectrum line is proportional to the concentration of species to be detected.

There are many spectrometers available on the market. Most of them use precision diffraction gratings and expensive precision mechanics to achieve their performance. These spectrometers are rather large and expensive devices which can be used for detection of a signal from optical fiber sensors in laboratory, but not in field conditions. Moreover, for operation of most fiber optic sensors it is not necessary to have complete spectrum of the radiation. The spectrum analyzer could be tuned to one or two specific lines of spectrum, i.e. to the fingerprint of the specific species to be detected. For this and other applications it is desirable to have a compact inexpensive spectrum analyzer which can be easily adjusted to each specific spectrum line.

A miniature fiber optic spectrometer S-1000 has been recently developed by Ocean Optics, Inc. for operation in UV, VIS and NIR ranges of spectrum This spectrometer, however, is not able to operate in Middle Infrared (MIR) range of spectrum which is the most important region for chemical sensors operation, since the most useful fingerprints of many materials are located just in this range of the spectrum In a recent paper by D. D. Marcenac and J. E. Carroll ("Maximum-entropy optical spectrum analyzer" Optics Letters 20, (1995) 1074–1076) a new type of spectrometer is demonstrated which has no movable parts, no additional optical source and no precision engineering. The spectrometer operates by transmitting the laser fight through two single-mode fibers to generate an interference pattern in the far field whose brightness is shown to be a measure of a optical signal's autocorrelation. The interference pattern is captured with an infrared camera using a charge coupled device (CCD) and is transferred to a computer. The computer is used for numerical processing of information in order to extract the spectrum of the light form the interference pattern. This spectrum analyzer, however, can not operate on real time scale as is desirable for many sensing applications. It also can not operate with multimode waveguides generating a complicated speckle pattern (modal noise) which disturbs the signal interference pattern.

As a result, this spectrum analyzer can not be used in the middle infrared range of spectrum where single-mode fibers are still not available.

OBJECTS AND SUMMARY OF THE INVENTION

It is an object of the present invention to provide a simple spectrum analyzer which can operate on a real time scale and does not require complicated computer processing of information.

Another object is to provide a spectrum analyzer which can operate in UV, VIS, NIR as well as in Middle Infra Red (MIR) range of spectrum.

Still another object is to provide a spectrum analyzer compatible with multimode waveguides which can better capture the signal optical beam than single-mode waveguides for its applications with optical fiber sensors.

Briefly stated, the present invention provides an optical spectrum analyzer based on optical processing of the far field interference pattern from two beams irradiated by light transmitting fibers. The spectrum analyzer can operate in UV, VIS, NIR and MIR ranges of spectrum and it can be based on either optical fibers (multimode or single-mode) or integrated optical waveguides. It can find many important applications in simple, compact and inexpensive fiber optic chemical and biological sensors.

The above, and other objects, features and advantages of the present invitation will become apparent from the following description read in conjunction with the accompanying drawings.

DESCRIPTION OF PREFERRED EMBODIMENTS

Figure 1:
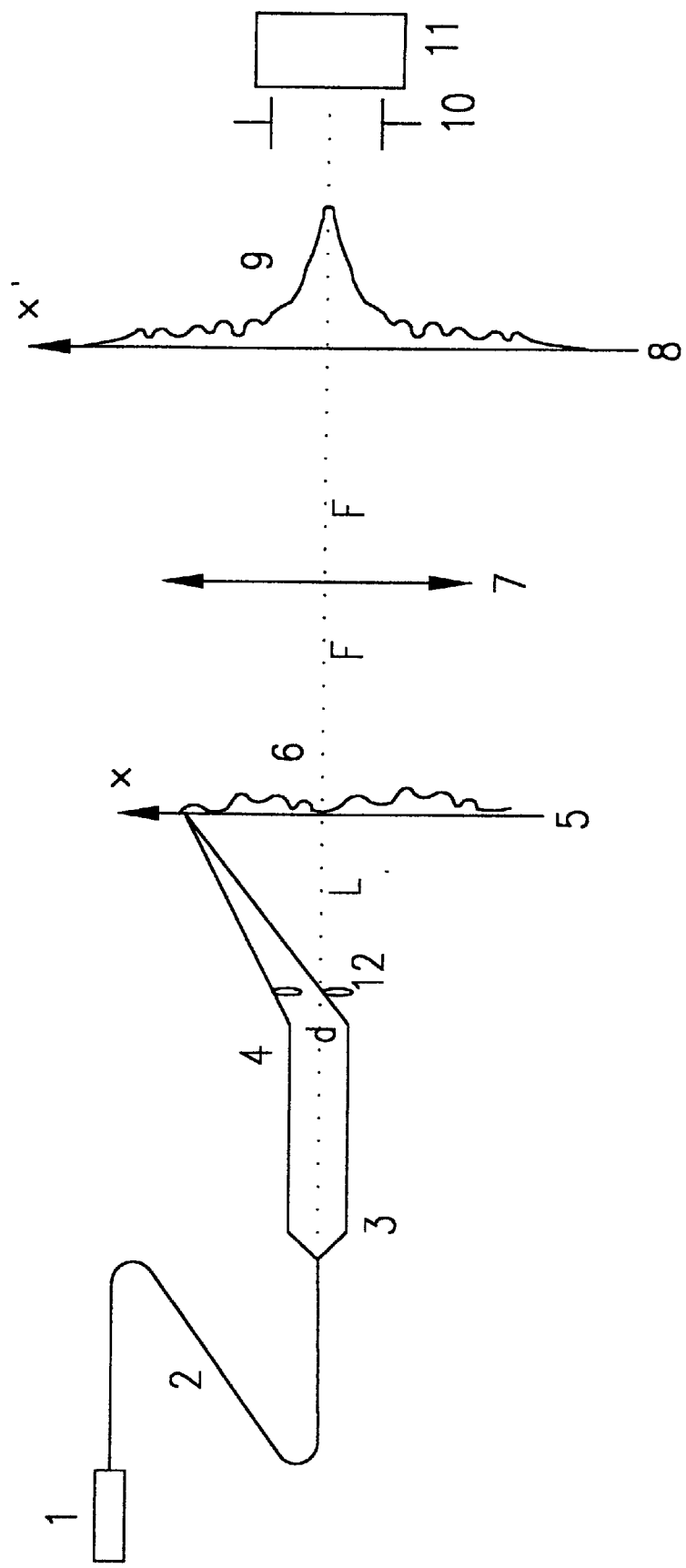
FIG. 1 shows a schematic of the optical fiber spectrum analyzer.

The present invention describes a new spectrum analyzer compatible with light transmitting optical fibers. FIG. 1 shows one preferred embodiment of such a spectrum analyzer.

A light signal from source or sensor 1 whose spectrum is to be analyzed is delivered by optical fiber 2. The output end of fiber 2 has Y-junction 3 which splits the delivered light beam into two parts having equal powers. End faces 4 of optical fiber Y-junction 3 are spaced apart by some distance d. Core cross section of the fibers in Y-junction 3 play a role of pinholes. Far field interference pattern 6 in plane 5 at distance L from the ends of Y-junction 3 is a direct measure of the autocorrelation function of light signal 1: $C(x) \cong <E(t) E(t+\tau)>$, with $\tau \cong x(d/Lc)$, where E is an electric field component, x is transverse coordinate, c is the velocity of light, $T\tau$ is time delay and t is the time variable. The optical power spectrum $P(\omega)$ is the Fourier transform of the autocorrelation function and it can be determined as follows:

$$P(\omega) = \int C(\tau) \exp(-i\omega\tau) d\tau, \qquad (1)$$

Integration in expression (1) should be performed over whole transverse coordinates x since $\tau \cong x(d/Lc)$.

Lens 7 having focal length F performs a Fourier transformation of interference pattern 6 if it is placed at the same distance F between interference plane 5 and output optical plane 8. Thus, intensity distribution 9 over transverse coordinate x' in output plane 8 is proportional to the spectrum of input light signal 1 to be analyzed. Specific lines of this spectrum can be selected with the help of aperture 10 and then detected by detector 11. Alternatively, a standard CCD detector or a camera can also be employed for complete detection of power distribution over the spectrum of radiation and for spatial selection of specific lines of the spectrum This detector can be connected to a computer providing a possibility for multichannel processing of incoming optical signal corresponding to different wavelengths of radiation.

The capability of direct optical processing (Fourier transform) of interference pattern 6 in plane 5 on a real time scale without employing a computer for numerical processing of the signal is a great advantage of this spectrum analyzer over that proposed by Marcenac and Carroll.

Another advantage is a possibility of miniaturization of the spectrum analyzer of the present invention. In the spectrum analyzer proposed by Marcenac and Carroll distance L between fiber end faces 4 and interference pattern 6 was sufficiently large (more that 70 cm) as well as the distance d (about 2 cm) between fiber end faces 4. The distance between interference flinges in the far field is proportional to $(\lambda/d)L$, where $\lambda$ is wavelength of radiation. Therefore, such large distance (d=2 cm) provided sufficiently large number (300) of diffraction fringes captured by the infrared camera (without its objective) used to record the far field interference pattern. Small core cross sections of the single-mode fibers used in this spectrum analyzer, which are comparable with wavelength of radiation, play the role of output pinholes providing efficient divergence of the beams as a result of their diffraction. Distance L from the fiber end faces to the far field interference plane was chosen to provide efficient overlap of the diffraction patterns from each pinhole and to ensure that the single pinhole diffraction pattern does not significantly disturb the required two-pinhole interference pattern. Large dimensions of the system complicate fabrication of miniature spectrum analyzers as are desirable for operation with many optical fiber sensors.

For miniaturization of the optical fiber spectrum analyzer described above it is important to make distance L as small as possible. To reduce this distance, one can increase angular divergence of the beams irradiated by fibers using suitable optics 12. For example, the angular divergence of the beams irradiated by two end faces of the optical fiber Y-junction can be increased with the help of nicrolenses or graded-index lenses. In one preferred embodiment a section of multimode graded-index fiber connected to end face of the fiber can be employed as a miniature graded-index lens. The same effect of increasing angular divergence of the beam irradiated by two fiber end faces may be achieved by polishing the fiber end faces to provide them with an appropriate lens-like shape.

Employing lens 7 which performs the Fourier transformation also offers a simple solution of the miniaturization problem. In the case of optical processing of interference pattern 6 the optical signal must be detected not in the far field interference plane 5 but in Fourier transform plane 8 where only part of the image corresponding to useful signal is to be captured by the detector aperture or a camera. The image in the far field interference plane can be very large enabling miniaturization of the system (small distance between fibers d and small length L). We have here a very favorable situation. The larger the image of the interference pattern in plane of image 5 the smaller the size of its Fourier transform in Fourier plane 8 where the signal is detected. The signal image in Fourier transform plane can remain, however, large enough to provide good optical resolution. This useful property of optical Fourier transformation is essential to miniaturize the spectrum analyzer. Spectrum analyzer proposed by Marcenac and Carroll has still another disadvantage. It is based of single-mode fibers. The light coupling efficiency into single-mode fibers is usually very low due to small cross section of the fiber core. This essentially restricts potential applications of such spectrum analyzers. In many practical applications when a spectrum of weak optical signals are to be analyzed it is desirable to employ multimode fibers having larger core cross section for transmission of the signals. Moreover, the single-mode fibers are not yet available for MIR range of spectrum where the most important fingerprints of many species are located. Therefore only multimode MIR fibers can be used for MIR spectroscopy and different MIR sensors.

The far field pattern of the beam irradiated by typical multimode fiber has a speckle pattern resulting from interference of various fiber modes arriving to output fiber end face with different phases. Dynamical variation of the speckle pattern as a result of random changing of the phase relations between different modes is known as the modal noise. Therefore, in the case of employing multimode fiber 2 and multimode Y-junction 3 interference pattern 6 is disturbed by the speckle pattern (modal noise). The number of speckles is proportional to the number of waveguide modes and their size is inversely proportional to this number. Therefore for sufficiently large number of modes in multi-mode fibers the fringes in interference pattern 6 in plane 5 are destroyed by a very large amount of small size speckles. These speckles would make numerical processing of the interference pattern in the spectrum analyzer proposed by Marcenac and Carroll virtually impossible. In the spectrum analyzer of the present invention, a Fourier transform image of the regularly spaced interference fringes is located in the central region of Fourier plane 8, while small modal noise speckles contribute to outer region of the Fourier image. Using aperture 10 with regular photodetector 11, CCD detector or camera, one can conveniently separate the useful signal describing the power distribution as a function of the radiation frequency from modal noise. This is another important advantage of the optical means of processing interference pattern proposed in the present invention over the computer approach.

Aperture 10 selecting desired sections of optical signal in Fourier transform plane can be replaced by an optical fiber. Small cross section of the fiber input end face can be used instead of aperture 10. Such a fiber will collect the light signal from desired section of the Fourier transform image and transmit it to detector 11. A microlens or a graded index lens can also be used at the fiber input end face to improve the light coupling efficiency. Moreover, a number of such optical fibers can be used to select specific sections of the Fourier transform image corresponding to desired wavelength and to transmit their signals to a number of photo-detectors 11. Multichannel processing of optical signals corresponding to different wavelengths can be performed in such a way.

The optical fiber spectrum analyzer described above is based on quite general principles. It generally comprises a means to deliver test light whose spectrum should be analyzed. The test light beam is divided then into two beams having preferably equal powers. Overlapping of these beams results in a far field interference pattern. The system has also an optical means to perform Fourier transform of the far field interference pattern and detector which can selectively detect the desired sections of Fourier transformed optical image. The detector may be connected to a computer for multichannel processing of the optical signal.

In some specific applications, for miniaturization of the spectrometer and increasing spacing between far field interference fringes, it may be desirable to bring two fibers together as close as possible. The distance between two fibers, however, can not be made smaller than the fiber diameter. In one preferred embodiment of the miniature spectrum analyzer one can employ one single multimode fiber and selectively excite two different modes inside this fiber using suitable optical means. Far field interference between these two modes irradiated by the fiber output end face results in well spaced interference flinges. This is provided by the small distance between two beams corresponding to different modes in the same multimode fiber. Special spatial filters, computer generated or physical holograms can be used for selective excitation of different specific modes in a multimode fiber. The same computer generated hologram corresponding to a superposition of two specific waveguide modes can be also used at the fiber output to ensure better selection of the desired fiber modes. The selective excitation and detection of specific modes inside multimode fiber with the help of modal filters and computer generated holograms is an experimentally demonstrated technique.

Another possibility to design a miniature spectrum analyzer is to side polish the cladding of the fibers at their output ends in order to bring the light emitting fiber cores as close as possible. One can employ also a special double-core fiber having two cores surrounded by common cladding. The distance between these two cores can also be made much smaller than the distance between individual fibers. Each of the cores in the double core fiber may be flat having a rectangular or elliptical cross section. Such shape of the cores provides still smaller spacing between them. Special optical means can be used for efficient excitation of such double core fiber. In one preferred embodiment one can employ a Y-junction made from standard fibers which can be effectively excited using standard light coupling optics. Two branches of this Y-junction are combined then into a single double-core output fiber in such a way that each branch is coupled only into one core of the double core fiber. This prevents destructive interference of two optical beams coming from different branches of the Y-junction. The double core fibers can be fabricated either by drawing them from a special preform having two core sections of corresponding shape, or by fusing together two output ends of standard fibers.

Figure 2:
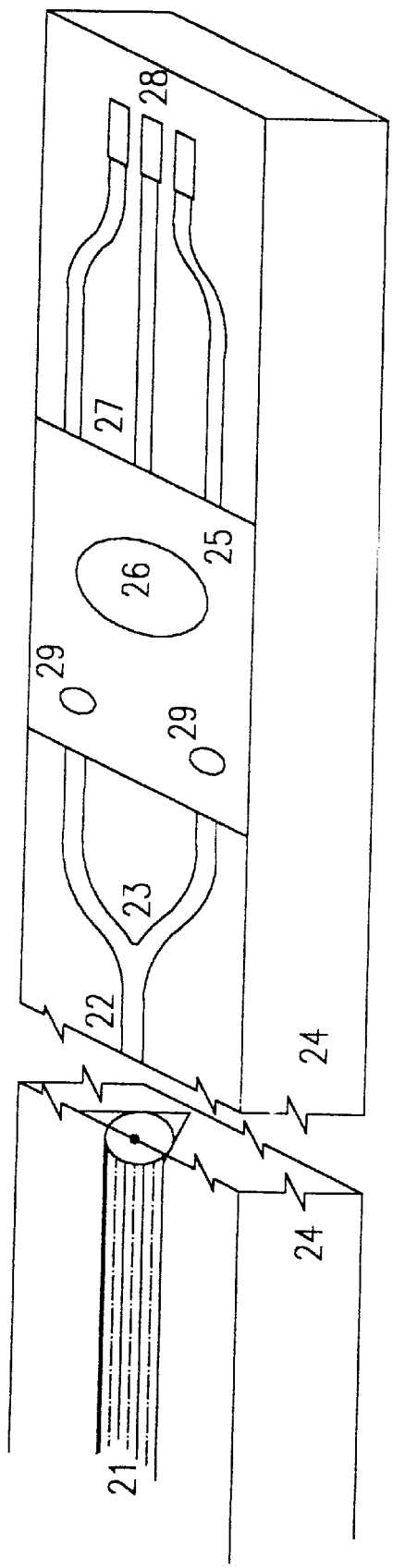
FIG. 2 shows a schematic of the integrated optical spectrum analyzer.

In another preferred embodiment a miniature optical spectrum analyzer can be fabricated using integrated optical technology, as shown in FIG. 2. Signal light delivered by optical fiber 21 is coupled into integrated optical waveguide 22 which splits the test beam into two parts with the help of Y-junction 23. Integrated optical waveguide 22 and Y-junction 23 are fabricated on the same substrate 24. For example, to provide efficient coupling the light from delivering fiber 21 into integrated optical waveguide 22 having a rib shape one can butt-join fiber and waveguide using well developed V-groove technology.

Each of two ends of integrated optical Y-junction irradiates light into planar integrated optical waveguide 25. This waveguide has integrated optical lens 26 performing Fourier transform of the interference pattern from two waveguide ends. Integrated optical waveguide 27 is used to select a specific line in Fourier transform image corresponding to desired frequency to be detected and to transmit the light signal to integrated optical detector 28. Additionally, two integrated optical lenses 29 can be used to increase the angular divergence of the beams irradiated by the ends of Y-junction. A number of such waveguides and detectors can be used to detect signals corresponding to different frequency components of radiation and for multichannel processing of the signals. Integrated optical microlenses can also be employed to improve coupling of the light signals from selected sections of the Fourier transformed image into the detector or output waveguides transmitting the light signals to the detectors.

Optical spectrum analyzers described in the present invention can operate in a very broad range of spectrum: from ultraviolet (UV) through visible (VIS) and near infrared (NIR) to Middle infrared (MIR) ranges. Different optical materials should be employed, however, for each specific wavelength of operation. For example, fiber optic spectrum analyzers for operation in UV, VIS and NIR ranges of spectrum can be based on various silica fibers and they can employ standard optical lenses.

One of the most important advantages of the optical spectrum analyzer proposed in this invention is its ability to operate in MIR range of spectrum This range of spectrum just corresponds to a "finger-print region" of spectra for fundamental molecular vibrations. Therefore spectrum analyzers for MIR range of spectrum will have many important applications in conjunction with different chemical and biological optical sensors.

To design fiber optic spectrum analyzers operating in MIR range of spectrum one must employ, however, optical fibers made from special materials which are transparent in the MIR range of spectrum. Such fibers are well known and have found many important applications in spectroscopic measurements and sensors. They can be based, for example, on silver halide mixed crystals, $AgCl_xBr_{1-x}$. Silver halide fibers are extruded from single crystals and have a polycrystalline structure. These fibers are flexible, water insoluble, and non-toxic and have good transmission in middle infrared region (3–25 $\mu$m).

Y-junctions made from MIR fibers are also known to exist. ZnSe lens can be employed as an optical element performing Fourier transformation in the system There are quite a number of different MIR optical fiber probes which can be employed in the optical fiber sensors. These probes are known to have various designs. They can be based on MIR fiber Y-junction one branch of which transmits light form a light source to a sample to be analyzed while another branch receives the light reflected from the sample and transmits it to spectrum analyzer. The probe may comprise also an optical element for an attenuated total reflection or evanescent sensing element attached optically to light transmitting fiber of the sensitive probe. The sensitive element may be designed as a double or multiple pass transmission gas or fluid cell with a mirror inside a cell to reflect source signal beam coming from a fiber back through a cell to return it to a fiber delivering the beam to the spectrum analyzer. Combination of all these sensitive MIR fiber probes with spectrum analyzer of the present invention results an a new family of chemical and biological sensors.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A compact, all-optical spectrum analyzer for use with fiber optic chemical sensors and biological sensors comprising:

means of accepting and delivering a signal light beam whose spectrum contains information about a chemical or biological species, being detected, and whose spectrum is to be analyzed;

a beam splitter accepting said signal light beam and splitting it into two output beams of substantially equal intensity and creating a far field interference pattern from said two output beams without using gratings;

an optical means for performing a Fourier transform of a far field interference pattern from said two output beams and projecting said interference pattern as an optical image into a Fourier transform plane;

an optical detector, said detector having means to select at least one section of said optical image within said Fourier transform plane; and means to analyze said optical image without computer analysis, on a real time scale, and to detect a chemical or biological species.

2. A compact, all-optical spectrum analyzer according to claim 1, wherein said beam splitter is an optical fiber Y-junction having two output end faces.

3. A compact, all-optical spectrum analyzer according to claim 2, wherein each of said two output end faces of said Y-junction has optical means to increase divergence of a beam irradiated by said fiber end face, said optical means to increase divergence of a beam irradiated by said fiber end face to be selected from a group consisting of a microlens, a graded index lens, or a prism, and said optical fibers having an appropriately shaped surface of their end faces.

4. A compact, all-optical spectrum analyzer according to claim 1, wherein said beam splitter comprises:

a multimode optical fiber having a means to selectively excite and to selectively detect two different modes inside said optical fiber;

said modes playing a role of two output beams;

said means to selectively excite two said modes is selected from the group consisting of light coupling optics, spatial filters, and computer holograms;

said means to selectively detect two said modes is selected from the group consisting of optics, spatial filters, and computer generated holograms, being used at an output end of said multimode optical fiber, to select two modes at said output end of said optical fiber and provide for their effective interference.

5. A compact, all-optical spectrum analyzer according to claim 1, wherein said beam splitter comprises at least one optical fiber having two cores, said double core fiber having means for efficient coupling of light into said two cores.

6. A compact, all-optical spectrum analyzer according to claim 1, wherein said beam splitter comprises a Y-junction splitting one input fiber into two branches and then combining them together into a single output fiber having two cores, light signal from each of said two branches of said Y-junction substantially coupled into separate cores of said double core output fiber.

7. A compact, all-optical spectrum analyzer according to claim 1, wherein said optical means to perform said Fourier transform being a lens.

8. A compact, all-optical spectrum analyzer according to claim 1, wherein said means for selection of a desired section of said optical image in said Fourier transform plane comprising an aperture.

9. A compact, all-optical spectrum analyzer according to claim 1, wherein said means for selection of at least one section of said optical image within said Fourier transform plane comprises a CCD detector.

10. A compact, all-optical spectrum analyzer according to claim 1, wherein said means for selection of at least one section of said optical image within said Fourier transform plane comprises at least two optical fibers, and said fibers transmit preselected signals to at least one detector providing means for multichannel processing of optical signals corresponding to different frequency components.

11. A compact, all-optical spectrum analyzer according to claim 10, wherein said at least two optical fibers have shaped end surfaces to improve efficiency of coupling light signals into said fibers.

12. A compact, all-optical spectrum analyzer according to claim 1, wherein a light signal from at least two sections of said optical image within said Fourier transform plane are focused individually onto said detector using a microlens or a graded-index lens.

13. A compact, all-optical spectrum analyzer according to claim 1, wherein said means of delivering a signal light beam comprises integrated waveguides, and said beam splitter is an integrated optical Y-junction having two output ends.

14. A compact, all-optical spectrum analyzer according to claim 13, wherein said Fourier transform is performed by an integrated optical lens.

15. A compact, all-optical spectrum analyzer according to claim 14, wherein said output ends of said integrated optical Y-junction have an optical means to increase divergence of light beam irradiated by said ends.

16. A compact, all-optical spectrum analyzer according to claim 15, wherein said optical means to increase divergence of beams irradiated by said ends of said Y-junction comprise integrated optical lenses.

17. A compact, all-optical spectrum analyzer according to claim 15, wherein said means for selection of at least one section of said optical image within said Fourier transform plane comprises at least two integrated optical waveguides, said waveguides transmitting preselected signals to at least one detector providing means for multichannel processing of optical signals corresponding to different frequency components.

18. A compact, all-optical spectrum analyzer according to claim 17, wherein a light signal from at least two sections of said optical image within said Fourier transform plane are focused individually onto an input end of said integrated optical waveguides, being used to select and transmit said signals to said detector.

19. A compact, all-optical spectrum analyzer according to claim 14, wherein a light signal from at least two sections of said optical image within said Fourier transform plane are focused individually onto said detector using an integrated optical lens.

20. A compact, all-optical spectrum analyzer according to claim 1, wherein materials and said means are selected to permit operation in the Middle Infra Red (MIR) range of spectrum where a majority of chemical and biological species have fingerprint spectra.

* * * * *